(12) United States Patent
Pimputkar et al.

(10) Patent No.: US 8,767,213 B2
(45) Date of Patent: Jul. 1, 2014

(54) DISHWASHER

(75) Inventors: Girish Pimputkar, Stockholm (SE); Per-Erik Pers, Mora (SE)

(73) Assignee: Electrolux Home Products Corporation, N.V., Brussels (BE)

( * ) Notice: Subject to any disclaimer, the term of this patent is extended or adjusted under 35 U.S.C. 154(b) by 353 days.

(21) Appl. No.: 13/127,162

(22) PCT Filed: Oct. 15, 2009

(86) PCT No.: PCT/EP2009/007409
§ 371 (c)(1),
(2), (4) Date: Jul. 15, 2011

(87) PCT Pub. No.: WO2010/051906
PCT Pub. Date: May 14, 2010

(65) Prior Publication Data
US 2011/0273714 A1    Nov. 10, 2011

(30) Foreign Application Priority Data
Nov. 4, 2008 (EP) .................................. 08019303

(51) Int. Cl.
*G01N 21/00* (2006.01)
*G01N 21/53* (2006.01)
*G01N 21/85* (2006.01)

(52) U.S. Cl.
CPC .......... *G01N 21/534* (2013.01); *G01N 21/8507* (2013.01)
USPC .............. 356/442; 356/73; 356/341; 250/573

(58) Field of Classification Search
USPC .................. 356/442, 339; 250/574
See application file for complete search history.

(56) References Cited

U.S. PATENT DOCUMENTS 3,888,269 A * 6/1975 Bashark ...................... 134/57 D
5,291,626 A * 3/1994 Molnar et al. ................ 8/158

(Continued)

FOREIGN PATENT DOCUMENTS

EP    1 475 471 A    11/2004

OTHER PUBLICATIONS

International Search Report from International Application No. PCT/EP2009/007409, filed Oct. 15, 2009.

*Primary Examiner* — Tarifur Chowdhury
*Assistant Examiner* — Isiaka Akanbi
(74) *Attorney, Agent, or Firm* — Alston & Bird LLP

(57) ABSTRACT

A turbidity sensor for use in a machine for washing articles, e.g., a washing machine (400). The turbidity sensor comprises a light source (210) for emitting light. The emitted light has a radiant intensity which is variable. The sensor further comprises a light-sensitive element (220) for receiving light emitted from the light source (210). The light source (211) and the light-sensitive element (220) are positioned relative to each other so that, when the light source (210) is in operation, light emitted from the light source (210) can propagate through a washing liquid contained in the washing machine (400) on its way to the light sensitive element (220). The light-sensitive element (220) is configured to measure the radiant intensity of light received at the light-sensitive element (221). Furthermore, the sensor comprises a controller (230) which is communicatively coupled to the light source (210) and the light-sensitive element (220). The controller (230) is configured to adjust the radiant intensity of the light emitted by the light source (210) in dependence of the measured radiant intensity of light received at the light-sensitive element (220).

15 Claims, 6 Drawing Sheets

(56) References Cited

U.S. PATENT DOCUMENTS

| | | | |
|---|---|---|---|
| 5,444,531 A * | 8/1995 | Foreman et al. | 356/341 |
| 5,467,187 A * | 11/1995 | Beers | 356/243.2 |
| 5,489,977 A * | 2/1996 | Winslow et al. | 356/73 |
| 5,560,060 A * | 10/1996 | Dausch et al. | 8/158 |
| 5,589,935 A | 12/1996 | Biard | |
| 7,060,979 B2 * | 6/2006 | Manz et al. | 250/343 |
| 2010/0195091 A1 * | 8/2010 | Fauth et al. | 356/51 |

* cited by examiner

DISHWASHER

CROSS REFERENCE TO RELATED APPLICATIONS

This application is a national stage application filed under 35 U.S.C. 371 of International Application No. PCT/EP 2009/007409, filed Oct. 15, 2009, which claims priority from European Application No. 08019303.0, filed Nov. 4, 2008, each of which is incorporated herein in its entirety.

TECHNICAL FIELD

The present invention generally relates to a turbidity sensor and a method of measuring the turbidity of a fluid. More particularly, it relates to a turbidity sensor for use in a machine for washing articles, e.g., a dishwasher or a washing machine.

BACKGROUND

Today, appliances or machines for washing dishware or clothes in a liquid medium may be equipped with sensors for measuring the turbidity. It is also possible to have a refrigerator with beverage dispensing system equipped with a sensor for measuring turbidity. As used herein the term turbidity generally refers to the concentration of light-scattering or light-absorbing particles suspended in the liquid medium. If turbidity increases in a fluid then, for a given wavelength, the transmittance generally decreases in dependence of, e.g.:

the wavelength,
the diameter distribution of the suspended particles,
the refractive index of the suspended particles, and
the surface properties of the suspended particles.

Settling particles and dissolved matter may also attenuate light travelling in the medium, but are generally not considered to contribute to turbidity. Knowledge of turbidity may be used, inter alia, for adapting various parameters of the washing cycle of the appliance to the degree of contamination of the articles to be washed. This may facilitate more economical use of resources, such as energy, water and detergent.

Turbidity sensors may be optical sensors positioned in a hydraulic path of the appliance and may measure the optical transmittance of the liquid medium at a certain wavelength. While generally a stable relationship exists between transmittance and turbidity for a specific type of particles, the quality of the turbidity measurements may be a limiting factor for the accuracy. A turbidity sensor may comprise a light source, such as a light-emitting diode (LED) or similar solid-state lighting device, and a light-sensitive element, such as a phototransistor. A portion of the light emitted by the light source can then be received by the light-sensitive element after passing through the liquid medium. By comparing the radiant intensity (radiated power per unit solid angle) $I_0$ of the emitted light and the radiant intensity I of the received light, it is possible to deduce the transmittance of the liquid medium, $$T = I/I_0. \quad (1)$$

The turbidity of the liquid can then be retrieved via an empirical transmittance-turbidity curve.

Generally, the accuracy of available turbidity sensors is satisfactory only in a narrow range. This shortcoming is partly due to the limited useful range of the light-sensitive elements used in the sensors. Indeed, the correlation between the output of the element and the radiant intensity of received light may degenerate when a saturation level is exceeded. Conversely, for intensities below the sensitivity threshold of the light-sensitive element, the signal may be drowned in noise and may thus be impossible or at least difficult to detect. Accordingly, it is understood that available turbidity sensors have some limitations.

SUMMARY

In view of the above, it would be desirable to achieve an improved sensor and/or method for measuring the turbidity of a fluid. In particular, it would be desirable to achieve a turbidity sensor having a wider operating range than previously available sensors. The sensor should, advantageously, have a simple and/or robust mechanical construction, and, further advantageously, be free of movable parts. Moreover, it would be advantageous to achieve a sensor which is durable and/or energy-lean.

To better address one or more of these concerns, as defined by the appended independent claims, there is provided a sensor, a machine, a method and a computer-program product for measuring the turbidity of a fluid.

In accordance with a first aspect of the invention, there is provided a turbidity sensor for measuring the turbidity of a fluid. The sensor comprises a light source for emitting light, the light having a radiant intensity which is variable, and a light-sensitive element for receiving light emitted from the light source. The light source and the light-sensitive element are positioned relative to each other so that, when the light source is in operation, light emitted from the light source propagates through a fluid on its way to the light sensitive element. Furthermore, the light-sensitive element is configured to measure the radiant intensity of light received at the light-sensitive element. A controller is communicatively coupled to the light source and the light-sensitive element. Moreover, the controller is configured to adjust, by selecting one intensity level out of a plurality of predetermined intensity levels, the radiant intensity of the light emitted by the light source in dependence of the measured radiant intensity of light received at the light-sensitive element.

The inventors have realised that a factor that may limit the accuracy of previously available turbidity sensors is the characteristics of typical transmittance-turbidity curves. FIG. 1 shows three examples of plots of transmittance T (in percent) as a function of turbidity Turb (in arbitrary units) in a range of interest. Available turbidity sensors may use a similar curve for recovering the turbidity of a liquid medium once its transmittance has been determined. Such a process is generally all the more sensitive to an error associated with the transmittance reading as the curve is flat, as expressed by the following elementary relationship between the turbidity error and transmittance error:

$$\Delta Turb = \frac{\Delta T}{dT/dTurb}. \quad (2)$$

In the two situations illustrated by curves A and B in FIG. 1, measurements with good accuracy are possible for low values of the turbidity, whereas both curves flatten for higher turbidity values. According to curve C, the transmittance decreases more rapidly towards the upper end of the interesting interval. In this case, however, low turbidity values are delicate to resolve, for the transmittance changes very little as the turbidity varies between 0 and 2 units.

However, the inventors have found that such turbidity sensors can be improved by making the radiant intensity $I_0$ of the light emitted by the light source selectable in dependence of the current turbidity. This can increase the resolving power of the sensor because the sensitivity to an error in the received light intensity I decreases. Indeed, combining equations (1) and (2) and applying the chain rule, one obtains $$\Delta Turb = \frac{1}{I_0} \frac{\Delta I}{dT/dTurb}. \quad (3)$$

Thus, increasing the intensity $I_0$ of the light emitted by the light source can make the turbidity measurements more accurate. Yet, to achieve an extension of the operating range of the turbidity sensor, it may be advantageous to control the emitted radiant intensity actively. Use of a high emitted radiant intensity throughout may otherwise cause saturation of the light-sensitive element at low turbidity.

The present invention is therefore also based on the inventors' further realisation that it is advantageous to adjust or regulate the radiant intensity of light emitted by the light source stepwise, that is, by selecting one intensity level out of a plurality of predetermined intensity levels. This is at least partly because the radiant intensity of light emitted by the light source can be known a priori with high accuracy. Then, for a given intensity of the emitted light, the transmittance can be obtained by multiplication by a constant factor, i.e., the inverse value of the intensity of the emitted light. In contrast with this, a sensor having a continuously adjustable light source would require further sensing means for assessing the actual radiant intensity of the emitted light.

The controller may further be configured to select a lower intensity level than the current intensity level if the measured radiant intensity of light received at the light-sensitive element exceeds an upper threshold value. The controller may further be configured to select a higher intensity level than the current intensity level if the measured radiant intensity of light received at the light-sensitive element is below a lower threshold value. Thus, the light-sensitive element may be associated with two threshold values, which provide the conditions for switching the light source to another intensity level. If the received light intensity is above the upper threshold value, then—if possible—a lower radiant intensity can be selected. If the received light intensity is below the lower threshold value, then—if possible—a higher intensity level can be selected. If the received light intensity falls between the threshold values—or if no further intensity levels are available—no action is taken.

The upper and lower threshold values may be determined in accordance with the sensitivity threshold and the saturation level of the light-sensitive element. Alternatively, or additionally, the threshold values can be established on the basis of the value of the derivative of the radiant intensity with respect to turbidity. In a particular embodiment, the lower threshold value $I_L$ can be determined, in part, by a condition on the derivative of the radiant intensity with respect to turbidity. Such a condition may be formulated as a lower bound on the derivative, e.g., $$I_L = \min\left\{I : \frac{dI}{dTurb} \geq C\right\}, \quad (4)$$

where C is a constant. Since the derivative in equation (4) is exactly the denominator of the right-hand side of equation (3), the condition of the received intensity dropping below the lower threshold value is equivalent to the error sensitivity rising above a predetermined level.

In one embodiment, the light-sensitive element is one from a group comprising a phototransistor, a photodiode and a photoresistor. Phototransistors and photodiodes are both capable of emitting a variable voltage responsive to the radiant intensity of light impinging on a light-sensitive surface. The resistance of a photoresistor varies in dependence of the intensity of light hitting a light-sensitive surface of the photoresistor. Hence, these components are suitable for measuring the radiant intensity of light.

In one embodiment, the sensor comprises a storage means for outputting a signal indicative of the turbidity of the fluid in dependence of the transmittance, as per equation (1). The storage means can be thought of as a table containing pairs of values of the transmittance and the turbidity. Alternatively, the storage means may output the signal indicative of the turbidity in response to the combination of the intensities of received and emitted light, I and $I_0$. In either case, the sensor may comprise means for interpolating between stored values.

In one embodiment of the invention, the light source of the turbidity sensor is a solid-state lighting device. For instance, the solid-state lighting device may be a LED. LEDs typically have a long lifetime and low power consumption and can, therefore, suitably be used as the light source of the turbidity sensor.

The light source may generate light in a portion of the visible spectrum (approximately 380-750 nm), suitably at or around green colour tones, or in the infrared or near-infrared range, preferably at or around a wavelength of 940 nm. In a further embodiment of the invention, the light-source of the turbidity sensor is adapted to emit light in a wavelength interval that is at least one of the visible spectrum, the infrared spectrum and the near-infrared spectrum.

In some embodiments of the invention, there is provided one or more means for favouring emission and/or reception along an optical path between the light source and the light-sensitive element. If preferred directions of the light source and the light-sensitive elements are aligned and perpendicular to the fluid interfaces, then the optical path can be thought of as a straight line. Such means for favouring transmission along the optical axis may include focusing lenses or lens assemblies and/or collimators, and may be provided either on the light-emitting side or the light-receiving side, or both. In one embodiment of the invention, a lens is provided after the light source, where it may focus light emitted by the light source. In one embodiment, a collimator can be provided before the light-sensitive element, where it may prevent light from reaching the light-sensitive element from other directions than a direct optical path from the light source.

In accordance with a second aspect of the invention, there is provided a machine for washing articles, such as dishware or textiles, comprising a turbidity sensor according to the first aspect described above. The machine may be a dishwasher or, alternatively, a washing machine.

In accordance with a third aspect of the invention, there is provided a method of measuring the turbidity of a fluid. The method comprises emitting light, having a radiant intensity which is variable, at a light source. The method also comprises receiving light from the light source, at a location to which the light propagates through the fluid, and measuring the radiant intensity of the light. Furthermore, the method comprises adjusting, by selecting one intensity level out of a plurality of predetermined intensity levels, the radiant intensity of light emitted by the light source in dependence of the measured radiant intensity of the light received at the light-sensitive element. An advantage of the method over previously available methods is that turbidity can be measured over a wide range of values, as explained above in connection with the first aspect of the invention.

In accordance with an embodiment of the third aspect of the invention, there is provided a method which further comprises selecting a lower intensity level than the current level if the radiant intensity of the received light exceeds an upper threshold value.

In accordance with an embodiment of the third aspect of the invention, there is provided a method which further comprises selecting a higher intensity level than the current level if the radiant intensity of the received light is below a lower threshold value.

Hence, by setting upper and lower threshold values, an operating interval of the light sensor can be defined.

In accordance with one embodiment of the invention, there is provided a method further comprising the steps of, firstly, dividing the radiant intensity value of the received light by the radiant intensity value of the emitted light, thereby obtaining a transmittance value, and, secondly, retrieving a turbidity value, corresponding to said transmittance value, from a storage means.

In one embodiment of the invention, there is provided a method comprising the steps described hereinabove, in which the lower threshold value is determined, in part, by a condition on the derivative of the transmittance with respect to turbidity. This can ensure that the error sensitivity is maintained at an acceptable magnitude.

Finally, in accordance with a fourth aspect of the invention, there is provided a computer-program product comprising software instructions which, when executed in an apparatus having computing capabilities, perform the method according to the third aspect of the invention.

In one embodiment, the computer-program product comprises computer program code means, comprising:

code means for emitting light, the light having a radiant intensity which is variable, at a light source;

code means for receiving light from the light source, at a location to which the light propagates through the fluid;

code means for measuring the radiant intensity of the received light; and code means for adjusting, by selecting one intensity level out of a plurality of predetermined intensity levels, the radiant intensity of the light emitted by the light source in dependence of the measured radiant intensity of the light received at the light-sensitive element.

The computer-program product may further comprise code means for selecting a lower intensity level than the current level if the radiant intensity of the received light exceeds an upper threshold value, and/or code means for selecting a higher intensity level than the current level if the radiant intensity of the received light is below a lower threshold value.

The computer-program product may further comprise code means for dividing the radiant intensity value of the received light by the radiant intensity value of the emitted light, thereby obtaining a transmittance value; and code means for retrieving a turbidity value, corresponding to said transmittance value, from a storage means. The lower threshold value may e.g. be determined, in part, by a condition on the derivative of the transmittance with respect to turbidity.

Generally, the second, third and fourth aspects may exhibit the same advantages and features as the first aspect.

These and other aspects of the invention will be apparent from and elucidated with reference to the embodiments described hereinafter.

Generally, all terms used herein are to be interpreted according to their ordinary meaning in the technical field, unless explicitly defined otherwise herein. All references to "a/an/the [element, device, component, means, step, etc.]" are to be interpreted openly as referring to at least one instance of the element, device, component, means, step, etc., unless explicitly stated otherwise.

BRIEF DESCRIPTION OF THE DRAWINGS

Embodiments of the present invention will now be described in more detail, reference being made to the enclosed drawings, in which.

DETAILED DESCRIPTION OF EMBODIMENTS

The present invention will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Furthermore, like numbers refer to like elements throughout.

Figure 2:
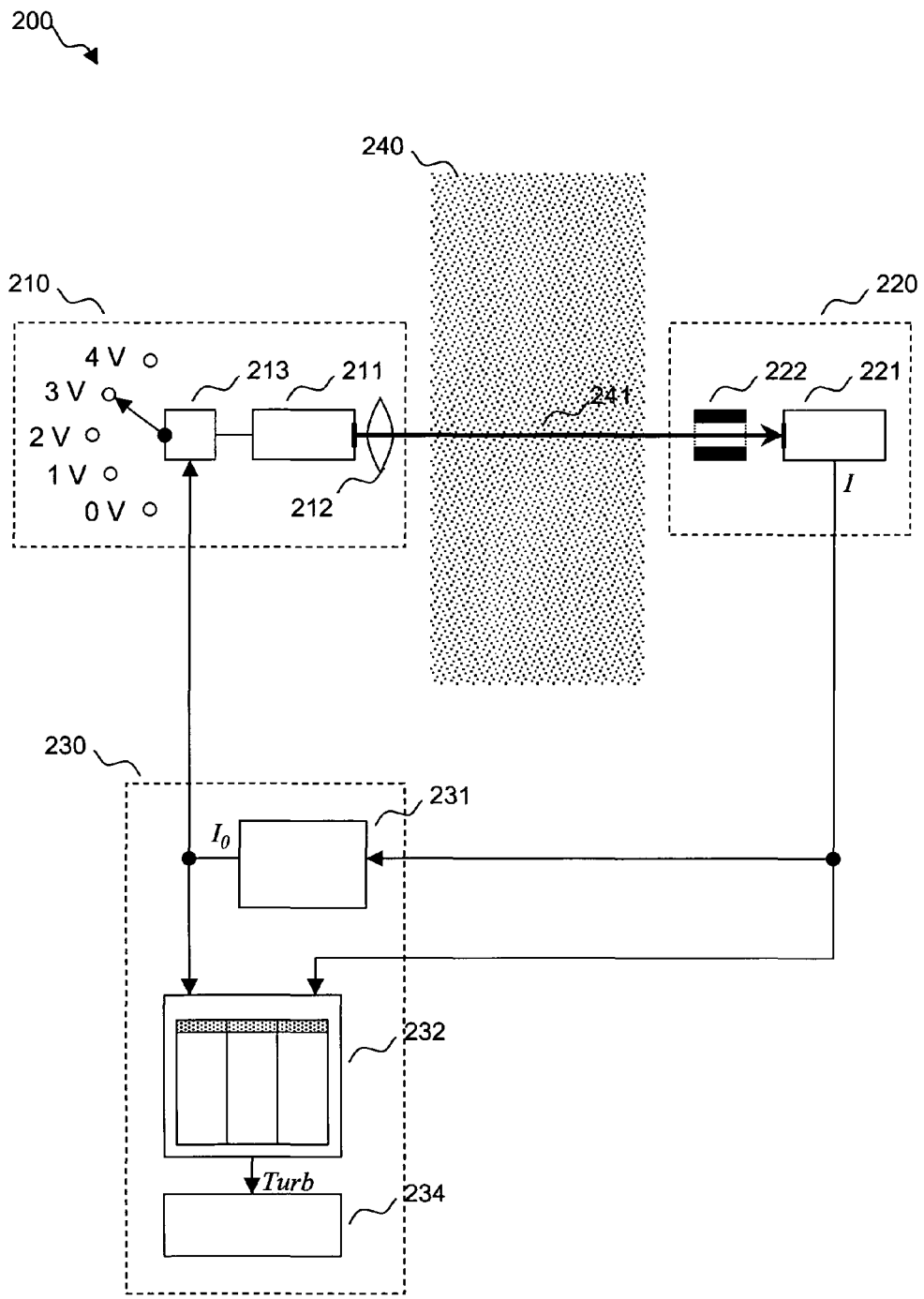
FIG. 2 is a block diagram of an optical sensor for measuring the turbidity of a fluid in accordance with an embodiment of the invention.

In accordance with an exemplary embodiment of the invention, FIG. 2 shows a sensor 200 for measuring the turbidity of a fluid 240. The sensor 200 according to this exemplary embodiment, which is here represented in block-diagram form, comprises a light-emitting portion 210, a light-receiving portion 220 and a processing and controlling portion 230. The light-emitting 210 and light-receiving 220 portions are so positioned that light emitted by the former, at least for the most part, can propagate through the fluid 240 to reach the latter. The processing and controlling portion 230 is configured to control the radiant intensity of light generated by the light-emitting portion 210 in dependence of the radiant intensity of light measured or detected by the light-receiving portion 220 and further to recover a turbidity value on the basis of the intensities of the emitted and received light.

It should be appreciated that the sensor 200 further includes a power supply section, and optionally a clock and similar auxiliary components. However, these and other components have been intentionally omitted from the drawings, since they are not necessary for explaining the principle of the invention and their addition is considered to belong to the general knowledge of the skilled person.

In the disclosed embodiment, the light-emitting portion 210 comprises a light source 211 and a focusing lens 212. As already stated above, the light source 211 may be subject to certain requirements regarding dimensions, reliability and power consumption, and is advantageously realised as a solid-state light source such as a LED. In the disclosed embodiment, the radiant intensity of light generated by the light source 211 is selectable by means of switch 213, which is controllable by means of the processing and control portion 230. In this example, the radiant intensity can be selected by actuating the switch 213 into one of four predetermined, fixed voltage levels. The switch 213 can also be set to zero voltage, which is equivalent to deactivating the light source 211.

If the turbidity sensor 200 is incorporated in, e.g., a washing machine, the zero voltage position may be the predominant mode in terms of time. Indeed, a turbidity measurement can be effectuated in a period of the order of one second, and typically, enough information for controlling a washing cycle can be extracted from less than ten measurements over the washing cycle. Accordingly, the light source 211 may be subject to negligible fatigue and wear during the lifetime of the washing machine and will not deteriorate noticeably as regards its radiated intensity. Therefore, some of those skilled in the art may consider that there is little need to monitor the actual intensity emitted by the light source 211 when the sensor 200 is used in a washing machine or similar appliance. In situations where the light source 211 is active over a larger portion of time—this may be the case, e.g., in some professional appliances—a calibration procedure may be effectuated at regular intervals. The clean state of the washing fluid at the beginning of a washing cycle may be used as a reference, e.g. representing a minimal turbidity level.

In the disclosed embodiment shown in FIG. 2, the focusing lens 212 serves as a relatively simple means for collecting the light beams emitted by the light source 211 into a parallel beam. Several alternative focusing means could be envisaged, such as a collimator or an assembly of several lenses. The light emitted by the light source 211, at a radiant intensity $I_0$, may propagate along an optical path 241, a portion of which intersects the fluid 240, and is eventually received by the light-receiving portion 220. Along the optical path 241, optical attenuation (which may, e.g., be the result of dissipation caused by the fluid or by absorbing matter which is dissolved or suspended therein) may take place along with scattering in various directions. Due to attenuation and scattering, the light beam may exit the fluid with a lower intensity I, from which an effective transmittance can be computed as per equation (1).

Still with reference to the exemplary embodiment disclosed in FIG. 2, the light-receiving portion 220 comprises a light-sensitive element 221, which may suitably be a phototransistor adapted to receive light in a wavelength range that is compatible with the light source 211. To prevent re-scattered light from exciting the light-sensitive element 221, this latter may advantageously be preceded by a collimator 222 which cuts out light not impinging substantially on the optical axis 241. A signal that encodes the radiant intensity of the received light I can then be provided to the processing and controlling portion 230. A controller 231 is configured to check whether the intensity of the received light lies between an upper and a lower threshold value. When suitably chosen the threshold values indicate, on the one hand, an optimal operating range of the hardware of the light-sensitive element 221 and, on the other, a range in which the accuracy of the instrument as a whole can be expected to be satisfactory considering the actual transmittance-turbidity relationship, as previously discussed. If the intensity of light emitted by the light source 211 is not adequate, the controller 231 is configured to make an adjustment via the switch 213. In the embodiment shown in FIG. 2, the switch 213 is in the 3 V position, so that the intensity of the emitted light can be adjusted both upwards and downwards. If the switch 213 had been in any of the 1 V or 4 V positions, it would only have been possible to select, respectively, a higher and a lower intensity level.

Figure 1:
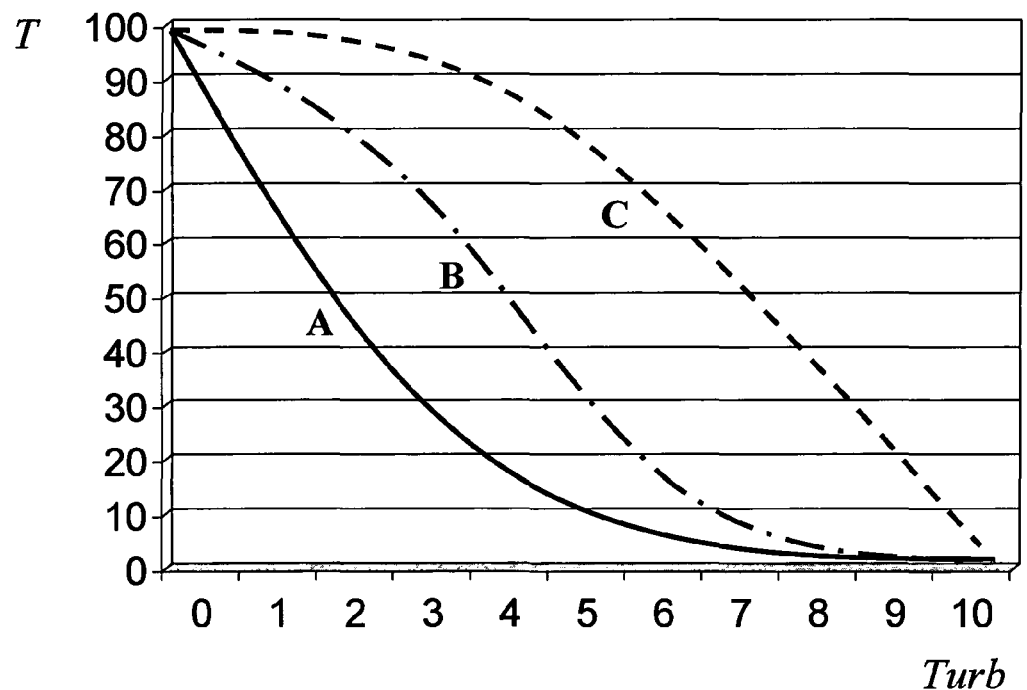
FIG. 1 is a graphical representation of the dependence of transmittance on turbidity in three exemplary cases.
Figure 3:
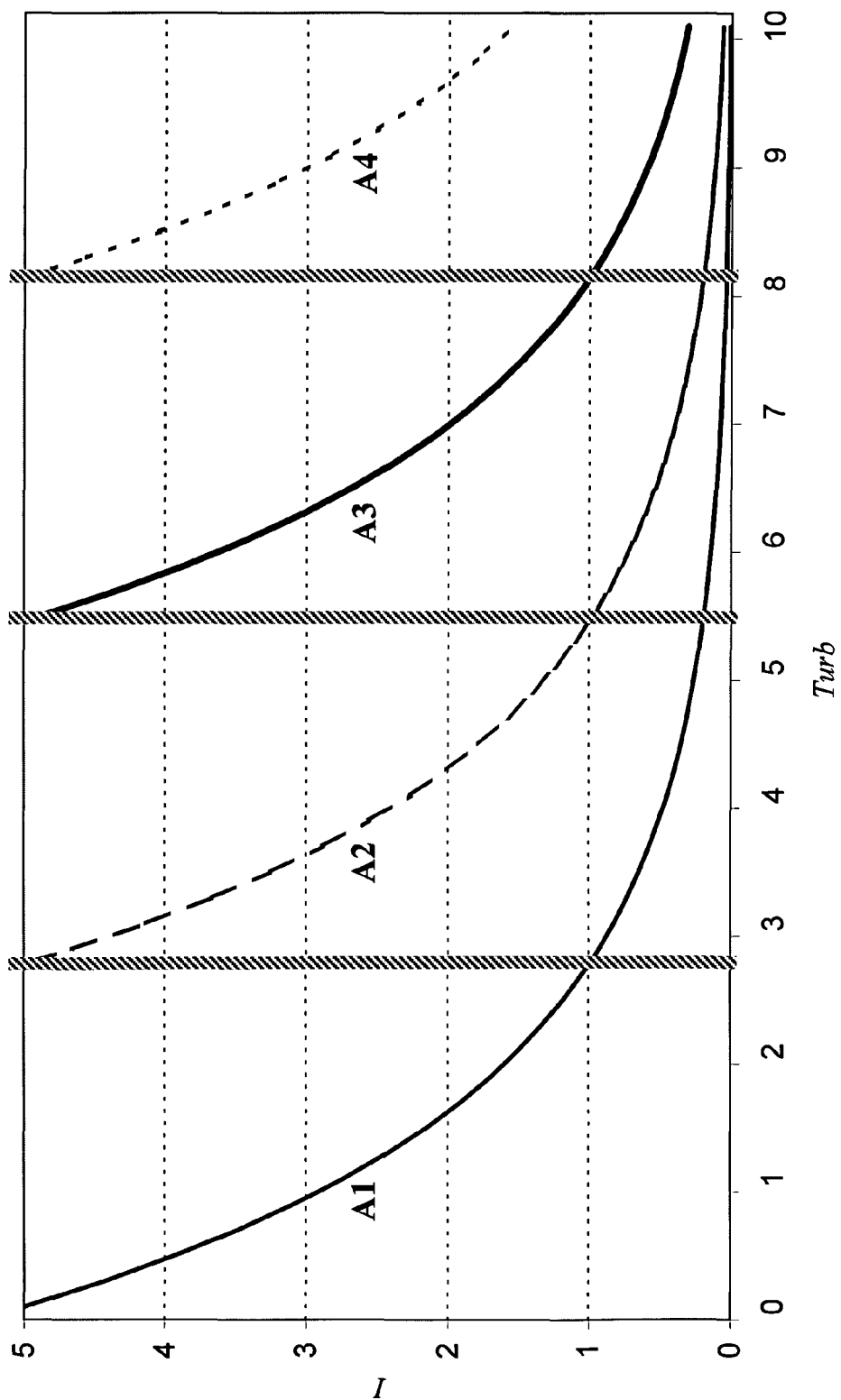
FIG. 3 is a graphical representation of the dependence of received intensity on turbidity for four different emitted intensities.
Figure 6:
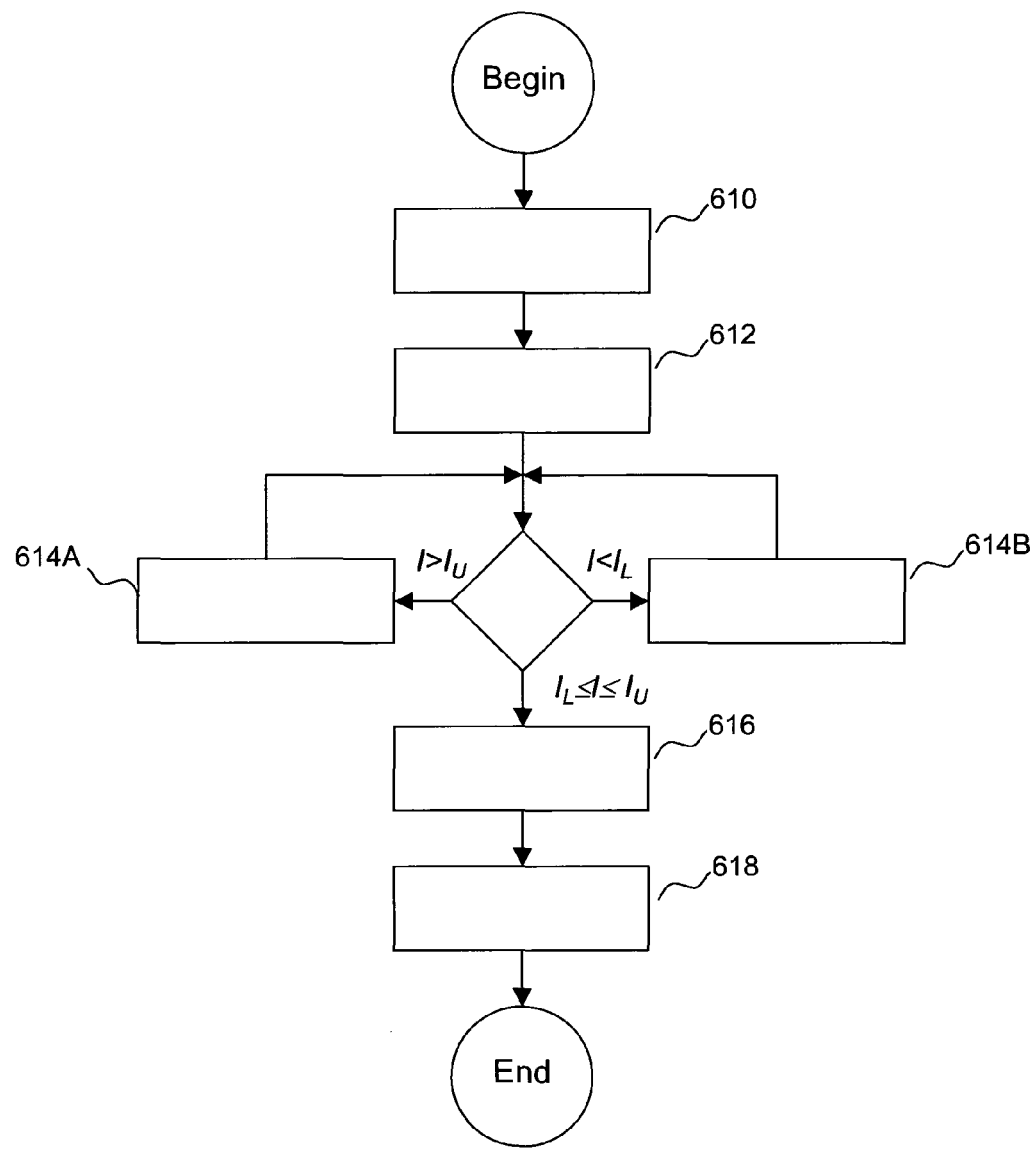
FIG. 6 is a flow chart of a method of measuring the turbidity of a fluid according to an embodiment of the invention.

FIG. 3 graphically shows the intensity of the received light as a function of the turbidity for each of four different levels of the intensity of the emitted light. To illustrate, it is supposed that the radiant intensity of the light emitted by the light source at the second level is 5 times the radiant intensity of the light emitted at the first level; the intensity associated with the third level is 25 times that associated with the first level; and the intensity associated with the fourth level is 125 times that associated with the first level. The intensity I (in arbitrary units) of the received light is represented by the vertical axis, whereas the turbidity Turb is represented by the horizontal axis (it is noted that FIG. 1, in contrast, is a transmittance-turbidity graph). The intensity $I_0$ of the emitted light may take four different values, and the corresponding measured values are represented by four curves A1, A2, A3 and A4. It is assumed that intensities of the received light between 1 and 5 units lie inside a preferred range of the light-sensitive element 221 of the turbidity sensor; hence, 1 and 5 can be taken as respective lower and upper threshold values. Accordingly, measurements of turbidity below approximately 2.7 turbidity units are performed with the light source 211 emitting light at the first intensity level (curve A1), turbidity measurements between approximately 2.7 and 5.4 units are performed at the second intensity level (curve A2), and so forth. As can be seen in FIG. 6, it would be possible to use both the first, second, third and fourth intensity level for performing measurements in the range from 5.4 and 8.1 turbidity units. However, using the fourth level (curve A4 is outside the graph) would saturate the light-sensitive element 221, whereas using the first or second level would imply an unfavourably high error sensitivity of the sensor 200 and/or unsuitably faint excitation (noisy signal) of the light-sensitive element 221.

Referring again to FIG. 2, a storage means 232 in the disclosed embodiment is configured to receive the two signals indicative of the radiant intensities of the emitted and received light and to return, on the basis of these, a signal indicative of the turbidity of the fluid to an output gateway 234. Alternatively, the instrument 200 may include a computing means (not shown) for calculating the transmittance; then the storage means 232 is configured to return a value of the turbidity on the basis of a transmittance value only. The output gateway 234 may be connected to a user display or to a regulating means forming part of a machine for washing articles. It may also be connected to a wired or wireless communication means (not shown) for transmitting the turbidity value to a receiver (not shown).

Figure 4:
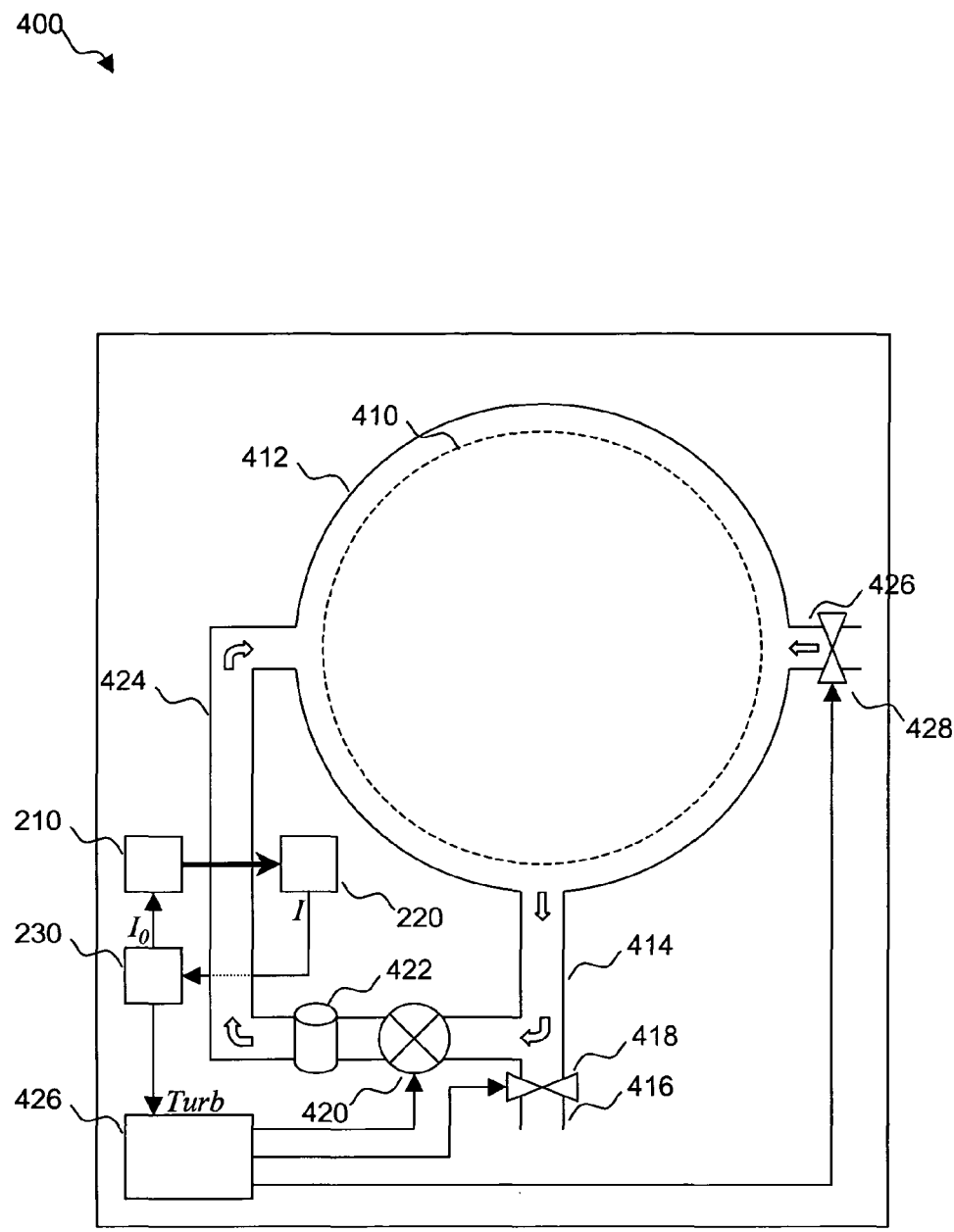
FIG. 4 shows a machine for washing textiles comprising the optical sensor of FIG. 2.

The sensor 200 may be used as an integrated part of a machine for washing dishware, textiles or other articles. To illustrate, FIG. 4 is a schematic view of an exemplary textile washing machine 400 having a drum 410 that is rotatable around its horizontal axis and permeable to washing liquid. The drum 410 is suspended in a basin 412 having a downward first duct 414 connected to a drain 416 via a first valve 418. During operation of the machine 400, the basin 412 generally contains an amount of washing liquid and the first valve 418 is in the closed position. Washing liquid is fed via an inlet 426 by opening a second valve 428. A pump 420 is adapted to recirculate fluid exiting the basin 412 via a second duct 424 preceded by a filter 422 for removing dirt particles larger than a certain size. Means for influencing the course of the washing cycle, notably the valves 418, 428 and the pump 420, are controllable by a control unit 426.

In this example, the sensor 200 described above is provided around the second duct 424 and provides a signal indicative of the turbidity to the control unit 426. The control unit 426 may then adapt the washing cycle according to the actual contamination of the textiles contained in the drum 410. More precisely, a light-emitting portion 210 of the sensor 200 is provided on one side of the second duct 424 and a light-receiving portion 220 is provided on the opposite side. A processing and controlling section 230 controls the light-emitting portion 210 and receives the measurement signal from the light-receiving section 220. After determining the turbidity of the fluid on the basis of the emitted and received intensities, the processing and controlling section 230 provides a signal indicative of the turbidity to the control unit 426. Advantageously, the walls of the second duct 424 are transparent to the wavelength of the light emitted by the sensor 200, at least in a segment around the sensor 200. Alternatively, apertures may be provided in the second duct 424, so that the light-emitting 210 and light-receiving portions 220 of the sensor 200 make direct contact with the washing fluid.

Figure 5:
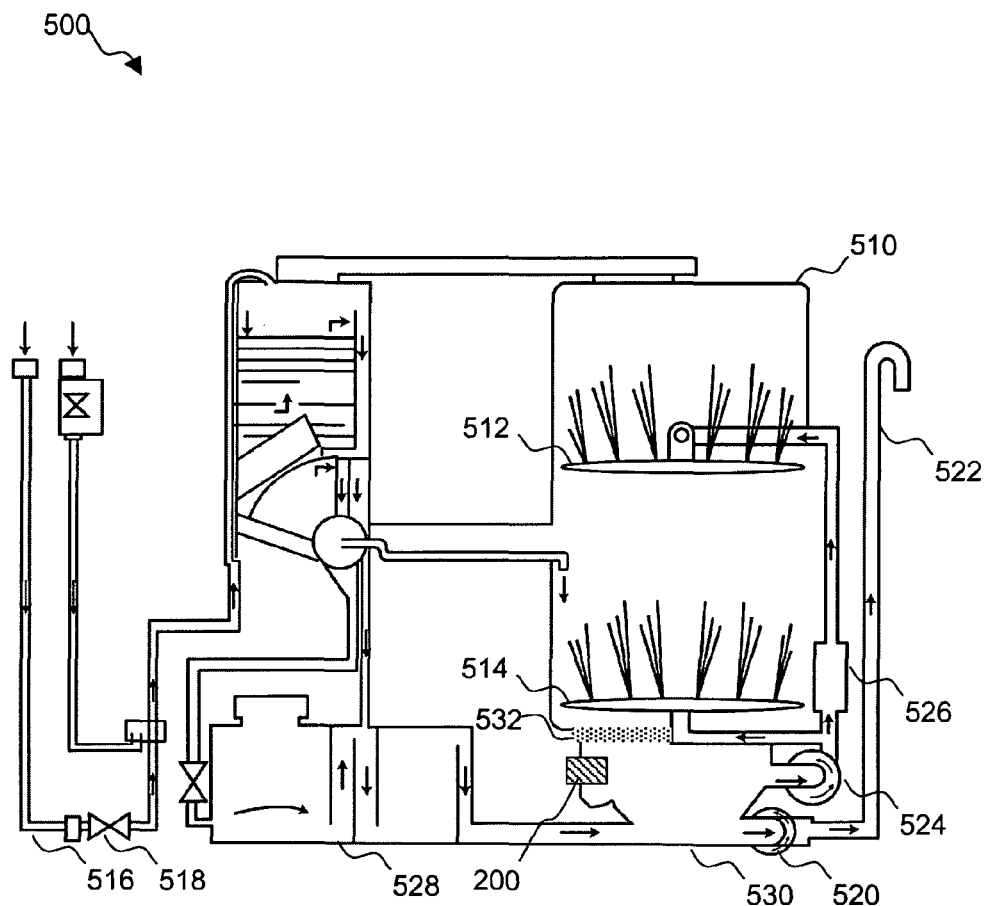
FIG. 5 shows a machine for washing dishware comprising the optical sensor of FIG. 2.

To further illustrate use of a turbidity sensor according to various embodiments of the invention, FIG. 5 is a schematic view of an exemplary dishwasher 500 having a dishware compartment 510, in which spray arms 512, 514 are arranged. Washing liquid, such as water, can be supplied via an inlet 516, at which a valve 518 is provided, and can be discharged via the outlet 522 by means of the drain pump 520. A system 528 for deliming is provided in the dishwasher 500. During operation, washing liquid is pressurised by the circulation pump 524 and is fed to the spray arms 512, 514 via a heater 526. After falling through the dishware compartment 510, the washing liquid reaches a sump 530 via a filter 532. In this embodiment, the turbidity sensor 200 according to the invention is located in the sump 530. The light-emitting portion (not shown) and the light-receiving portion (not shown) are provided at such locations relative to each other that any light emitted by the sensor 200 passes through the washing liquid. By its construction, notably by the placement of inlets and outlets, the sump 530 is generally liquid-filled up to a certain level during operation of the dishwasher 500. By placing both the light-emitting portion and the light-receiving portion of the turbidity sensor 200 below this level, a suitable optical path between these can be achieved.

It may be advantageous to place the turbidity sensor 200 downstream of the filter 532, because coarse particles are then removed and cannot perturb the measurement. It may further be advantageous to place the turbidity sensor 200 in a region of the sump 530 in which the current velocity during operation of the dishwasher 500 is relatively high, because this reduces the rate of deposition on light-emitting and light-receiving surfaces (not shown) of the sensor. It also ensures that the composition—and consequently the turbidity—of that washing liquid which is in contact with the sensor 200 (on which the measurements are based) is approximately identical to the composition of that washing liquid which is in contact with the dishware.

Alternatively, the turbidity sensor 200 can be placed around a portion of the hydraulic path between the sump 530 and any of the spray arms 512, 514. Similarly to the case of the washing machine 400, the light-emitting and the light-receiving portions of the turbidity sensor 200 may be arranged at either side of a liquid-filled duct.

A method 600 for measuring the turbidity of a fluid, is illustrated by the flowchart of FIG. 6. In the disclosed embodiment, the method comprises an initial step 610 of emitting light having an intensity $I_0$ which is variable. It is not essential which intensity level is used initially. In a second step 612, light emitted by the light source is received after having propagated through the fluid and its radiant intensity is measured. By assessing the intensity I of the received light with respect to an upper $I_U$ and a lower $I_L$ threshold value, it can be established whether the intensity level has been adequately chosen in relation to the turbidity of the fluid. If the intensity level turns out to be too high, a lower intensity level than the current intensity level is chosen (step 614A), and if it is too low, a higher intensity level than the current intensity level is chosen (step 614B). Subsequently, in step 616, the intensity I of the received light can be divided by the intensity $I_0$ of the emitted light to yield the transmittance, as per equation (1) above. In a final step 618, a measured turbidity corresponding to the computed transmittance can be retrieved from a storage means. In an alternative embodiment, a storage means containing triplets of values—intensity of emitted light, intensity of received light and turbidity—is used, so that steps 616 and 618 may be merged into one step.

The method 600 may be performed by software instructions included in a computer program product, which, as used herein, may be a computer-readable medium having software instructions stored thereon. By way of example, computer readable mediums may comprise computer storage media and communication media. As is well known to a person skilled in the art, computer storage media includes both volatile and non-volatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by a computer. Further, it is known to the skilled person that communication media typically embodies computer readable instructions, data structures, program modules or other data in a modulated data signal such as a carrier wave or other transport mechanism and includes any information delivery media.

While the invention has been illustrated and described in detail in the drawings and foregoing description, such illustration and description are to be considered illustrative or exemplary and not restrictive; the invention is not limited to the disclosed embodiment. It is understood that some components that are included in the disclosed embodiments are optional. For example, the focusing and collimating means may sometimes be superfluous; this is the case, at least, in embodiments having naturally collimated light-sources, such as certain types of lasers.

Other variations to the disclosed embodiments can be understood and effected by those skilled in the art in practicing the claimed invention, from a study of the drawings, the disclosure, and the appended claims. The mere fact that certain measures are recited in mutually different dependent claims does not indicate that a combination of these measured cannot be used to advantage. Any reference signs in the claims should not be construed as limiting the scope.

The invention claimed is:

1. A turbidity sensor for measuring the turbidity of a fluid, comprising:
   a light source for emitting light at an initial radiant intensity, wherein the initial radiant intensity is variable; and
   a light-sensitive element for receiving light emitted from the light source, the light source and the light-sensitive element being positioned relative to each other so that, when the light source is in operation, light emitted from the light source propagates through the fluid on its way to the light sensitive element, which light-sensitive element is configured to measure a received radiant intensity of light received at the light-sensitive element, wherein a controller is communicatively coupled to the light source and the light-sensitive element, the controller being configured to:
determine the initial radiant intensity of the light emitted by the light source; and
adjust, by selecting one intensity level out of a plurality of predetermined intensity levels, the initial radiant intensity for the light emitted by the light source to an updated initial radiant intensity based on the determined initial radiant intensity of the light emitted from the light source and the measured received radiant intensity of light received at the light-sensitive element.

2. A turbidity sensor according to claim 1, wherein the controller is further configured: to select a lower intensity level than the current intensity level if the measured radiant intensity of light received at the light-sensitive element exceeds an upper threshold value; and to select a higher intensity level than the current intensity level if the measured radiant intensity of light received at the light-sensitive element is below a lower threshold value.

3. A turbidity sensor according to claim 2, further comprising a storage means for outputting a signal indicative of the turbidity of the fluid in dependence of the transmittance, the storage means having stored therein pairs of transmittance and turbidity values, wherein the transmittance is the radiant intensity of light received by the light-sensitive element divided by the radiant intensity of light emitted by the light source.

4. A turbidity sensor according to claim 3, wherein said lower threshold value is determined, in part, by a condition on the derivative of the intensity with respect to turbidity.

5. A turbidity sensor according to claim 1, wherein the light-sensitive element is one from a group comprising: a phototransistor, a photodiode, and a photoresistor.

6. A turbidity sensor according to claim 1, wherein the light source is a solid-state lighting device.

7. A turbidity sensor according to claim 1, further comprising collimating means positioned at the light-sensitive element for excluding light not impinging directly from the light source.

8. A turbidity sensor according to claim 1, further comprising focusing means positioned at the light source for focusing light emitted by the light source.

9. A turbidity sensor according to claim 1, wherein the light source is adapted to emit light in a wavelength interval that is at least one of: the visible spectrum, the infrared spectrum, and the near-infrared spectrum.

10. A machine for washing articles, such as textiles or dishware, wherein the machine comprises a turbidity sensor according to claim 1.

11. A method of measuring the turbidity of a fluid, comprising:
emitting light at an initial radiant intensity, wherein the initial radiant intensity is variable, at a light source; and
receiving light from the light source, at a location to which the light propagates through the fluid, and measuring a received radiant intensity of the received light, determining the initial radiant intensity of the light emitted by the light source, and adjusting, by selecting one intensity level out of a plurality of predetermined intensity levels, the initial radiant intensity for the light emitted by the light source to an updated initial radiant intensity based on the determined initial radiant intensity of the light emitted from the light source and the measured received radiant intensity of the light received at the light-sensitive element.

12. A method according to claim 11, further comprising:
selecting a lower intensity level than the current level if the radiant intensity of the received light exceeds an upper threshold value, and selecting a higher intensity level than the current level if the radiant intensity of the received light is below a lower threshold value.

13. A method according to claim 12, further comprising:
dividing the radiant intensity value of the received light by the radiant intensity value of the emitted light, thereby obtaining a transmittance value; and retrieving a turbidity value, corresponding to said transmittance value, from a storage means.

14. A method according to claim 13, wherein said lower threshold value is determined, in part, by a condition on the derivative of the transmittance with respect to turbidity.

15. A non-transitory computer-program product comprising software instructions which, when executed in an apparatus having computing capabilities, perform the method according to claim 11.

* * * * *